United States Patent [19]
Frid et al.

[11] Patent Number: 5,857,967
[45] Date of Patent: Jan. 12, 1999

[54] UNIVERSALLY ACCESSIBLE HEALTHCARE DEVICES WITH ON THE FLY GENERATION OF HTML FILES

[75] Inventors: Marcos Frid, San Carlos; Thomas A. Shoup, Los Altos, both of Calif.

[73] Assignee: Hewlett-Packard Company, Palo Alto, Calif.

[21] Appl. No.: 890,727

[22] Filed: Jul. 9, 1997

[51] Int. Cl.$^6$ .................................................. G06F 159/00
[52] U.S. Cl. ........................... 600/301; 128/920; 128/904
[58] Field of Search ..................... 128/904, 920; 600/301; 395/187.01

[56] References Cited

U.S. PATENT DOCUMENTS 5,704,366  1/1998  Tacklind et al. ......................... 128/904
5,715,823  2/1998  Wood et al. .............................. 128/904

*Primary Examiner*—William E. Kamm
*Assistant Examiner*—Kennedy J. Schaetzle

[57] ABSTRACT

A universally accessible healthcare device having a communication path and a server. The healthcare device generates a set of medical information and the server provides access to the medical information using an open standard network protocol on the communication path. HTML Files may be generated on the fly by the server in response to an HTTP command from a requesting web client.

22 Claims, 2 Drawing Sheets

UNIVERSALLY ACCESSIBLE HEALTHCARE DEVICES WITH ON THE FLY GENERATION OF HTML FILES

BACKGROUND OF THE INVENTION

1. Field of Invention

The present invention pertains to the field of healthcare devices. More particularly, this invention relates to healthcare devices which are universally accessible using open standard network protocols.

2. Art Background

A variety of devices for obtaining medical information pertaining to patients are commonly employed in hospitals and clinics. For example, blood analyzers are commonly used in hospitals and clinics to obtain blood chemistry measurements such as glucose level. Other devices include devices for measuring heart rate, blood pressure, and devices for recording electrocardiogram data. Such devices are hereinafter referred to as healthcare devices. Such healthcare devices include portable devices such as portable blood analyzers, etc.

Prior healthcare devices commonly provide an access mechanism for transferring the medical information contained therein to a computer system. Such an access mechanism usually facilitates distribution of the medical information by taking advantage of the display and storage capabilities of a computer system.

The access mechanism of prior healthcare devices usually requires a computer system having a proprietary interface which is designed specially for the particular healthcare device. Typically, such a proprietary interface includes specialized software that executes on the computer system. Typically, a healthcare worker accesses medical information from such a prior healthcare device by transporting the healthcare device to the special computer system, attaching the healthcare device to a docking station or standard mechanism such as an RS232 port of the special computer system, and then initiating a transfer from the healthcare device using specialized software executing on the computer system.

Unfortunately, such prior methods of accessing healthcare devices are usually not well suited to out of hospital or out of clinic environments such as a patient's home where computer systems with proprietary interfaces are usually not available. Moreover, the costs associated with equipping a location such as a patient's home with a specialized computer system for accessing information from healthcare devices is usually prohibitively expensive.

Such limitations on the ability to access medical information in certain environments usually limits the utility of prior healthcare devices. For example, a visiting nurse may collect glucose data from a patient in the patient's home using a prior portable blood analyzer. Typically, the obtained glucose data remains stored in the portable blood analyzer until the visiting nurse returns to the hospital or clinic and manually initiates the transfer of the stored data to a special computer system. Unfortunately, a doctor cannot read the glucose data obtained with such a prior portable blood analyzer while it is in transit between the patient's home and the hospital.

SUMMARY OF THE INVENTION

One object of the present invention is to provide universal access to information stored in healthcare devices.

Another object of the present invention is to reduce the cost of home healthcare monitoring by eliminating the requirement of having a proprietary software package for accessing medical information from healthcare devices.

A further object of the present invention is to reduce the overall cost of home healthcare monitoring by eliminating the need for having a personal computer in the home to access medical information from healthcare devices.

Another object of the present invention is to make the medical information contained in healthcare devices widely accessible and available sooner in comparison to prior systems that employ proprietary interfaces to personal computers.

These and other objects are provided by a healthcare device having a communication path and a server. The healthcare device generates a set of medical information and the server provides access to the medical information using an open standard network protocol on the communication path. The server packages the medical information in an Hyper-Text Markup Language (HTML) file which is transported according to the Hyper-Text Transfer Protocol (HTTP). The server functionality may be implemented with existing circuitry in the healthcare device such as an exiting processor and memory that normally perform device-specific functions, thereby avoiding the extra cost and space required for dedicated server hardware for the healthcare device.

The server functionality embedded in the healthcare device enables a web browser to access the medical information obtained by the healthcare device via a variety of communication routes including the world wide web of the Internet. The HTML and HTTP protocols inherent in web technology enable communication with existing web browsers independent of the platform that executes the web browser and independent of the location of the healthcare worker that uses the web browser to access the medical information.

Other features and advantages of the present invention will be apparent from the detailed description that follows.

BRIEF DESCRIPTION OF THE DRAWINGS

The present invention is described with respect to particular exemplary embodiments thereof and reference is accordingly made to the drawings in which.

DETAILED DESCRIPTION

Figure 1:
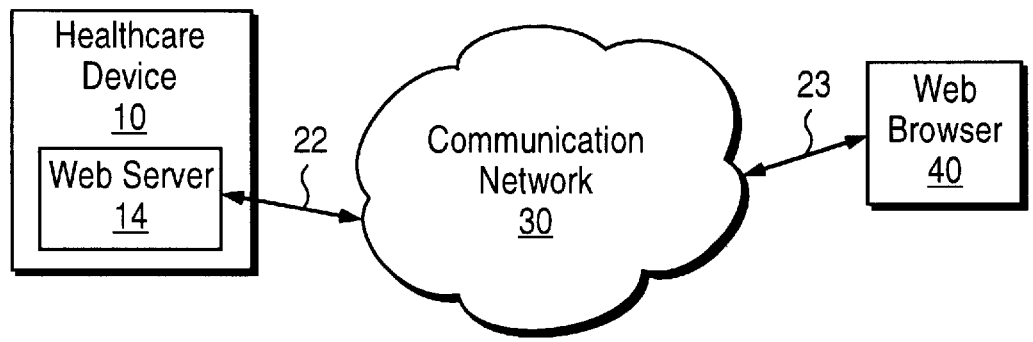
FIG. 1 shows a healthcare device which is universally accessible via a communication network using open standard network protocols.

FIG. 1 shows a healthcare device 10 which is universally accessible via a communication network 30 using open standard network protocols. The healthcare device 10 includes a web server 14 that exchanges messages with web clients using the HTTP and HTML open standard protocols on the communication network 30. The web server 14 handles HTTP commands received via the communication network 30 that specify a predetermined Universal Resource Locator (URL) for the healthcare device 10. The HTTP commands are used by web clients such as a web browser 40 to read medical information including measurement data and optional related information from the healthcare device 10. The web server 14 packages the medical information into the HTML format and transfers the information to requesting web clients on the communication network 30 using the HTTP protocol.

In one embodiment, the communication network 30 represents world wide web communication which is enabled by Internet communication protocols including HTTP and HTML. The healthcare device 10 and the web browser 40 use communication paths 22 and 23, respectively, for access to the Internet. The communication paths 22–23 may be direct Internet connections or connections to Internet Service Providers (ISPs) that in turn provide Internet access. The healthcare device 10 in this embodiment may be used to obtain measurements in a remote location from a hospital or clinic, such as a patient's home, and a doctor, nurse, or other healthcare worker located anywhere Internet access is available including a hospital or clinic may use the web browser 40 to access the obtained measurement data and related information from the healthcare device 10.

In another embodiment, the communication network 30 is a local area network that supports Internet communication protocols including HTTP and HTML as well as underlying layers including Transmission Control Protocol/Internet Protocol (TCP/IP). The communication paths 22–23 may be coaxial communication links, power line communication links, twisted pair communication links, radio frequency communication links, infrared communication links, or any combination thereof. The healthcare device 10 may be used to obtain measurements in a remote location of a hospital or clinic, such as a hospital ward, and a doctor, nurse, or other healthcare worker may use the web browser 40 located elsewhere in the hospital or clinic can access the healthcare device 10 via the local area network 30 of the hospital or clinic.

In yet another embodiment, the communication network 30 is a wide area network or "intranet" of a hospital, clinic, or large healthcare organization which can extend beyond the walls of the particular organization. The healthcare device 10 may be used to obtain measurements in one branch location of the healthcare organization or in a patient's home, and a healthcare worker may use the web browser 40 located in another branch of the healthcare organization to access information from the healthcare device 10 using the intranet 30 of the healthcare organization.

The web browser 40 may be embodied in a computer system that executes web browser software. Such a computer system with web browser functionality may be realized by any one of a variety of available computer system platforms including Windows platforms, Macintosh platforms, Unix platforms as well as any other platform capable of executing web browser software that provides HTTP client functions and that renders HTML files.

The web browser 40 may also be embodied in a variety of other devices that provide HTTP client functions and that render HTML files. Such devices include specialized hardware designed for television or telephone systems as well as low cost web browser devices and devices referred to as network computers.

A healthcare worker enters a URL corresponding to the healthcare device 10 into the web browser 40. In response, the web browser 40 transfers an HTTP command which includes the entered URL over the communication network 30. The HTTP command used by the web browser 40 to access medical information from the healthcare device 10 may be an HTTP GET, an HTTP POST, or an HTTP PUT command.

The web server 14 in the healthcare device 10 receives the HTTP command via the communication path 22 and recognizes the URL contained therein. In response, the web server 14 packages internally obtained medical information into an HTML file and transfers the HTML file containing the medical information to the web browser 40 using the HTTP protocol. The web browser 40 receives the HTML file and renders the medical information contained therein on a display.

In one embodiment, the healthcare device 10 is a portable blood analyzer. The healthcare device 10 includes modules for measuring aspects of blood chemistry such as glucose level as well as circuitry for storing blood chemistry measurement data in digital form. The healthcare device 10 also includes timing circuitry for generating time stamp data and further includes input circuitry such as a keypad that enables entry of patient identifiers and other related information for the obtained blood chemistry measurements. The web server 14 enables universal access to the blood chemistry data and related information via the communication network 30 using HTML and HTTP protocols.

In another embodiment, the healthcare device 10 is a portable electrocardiogram recorder having sensing mechanisms for obtaining electrocardiogram readings and electronic hardware and software for digitizing the recorded data. The web server 14 enables universal access to the recorded electrocardiogram data and related information using HTML and HTTP protocols. The patient can trigger data recording using a variety of triggering mechanisms or loops of electrocardiogram data may be recorded. The electrocardiogram device 10 may also provide real-time electrocardiogram data to an external web browser using HTML and HTTP protocols.

In another embodiment, the healthcare device 10 is a spirometer for measuring the efficiency of a patient's lungs. The web server 14 enables universal access to data indicating lung efficiency and related information stored in the healthcare device 10.

In yet another embodiment, the healthcare device 10 is a portable blood pressure measurement instrument. The healthcare device 10 includes mechanisms for measuring blood pressure as circuitry for storing blood pressure measurements. The web server 14 enables universal access to the blood pressure data and related information using HTML and HTTP protocols.

In another embodiment, the healthcare device 10 is a portable blood alcohol measurement instrument with mechanisms for measuring blood alcohol content as well as circuitry for storing measurements. The web server 14 provides universal access to the blood alcohol measurements and related information using HTML and HTTP protocols.

In another embodiment, the healthcare device 10 is a weight scale which is useful for monitoring changes in a patient's body weight. The healthcare device 10 includes mechanisms for weight measurement and circuitry for storing measurements. The web server 14 enables universal access to the weight measurement data and related information using HTML and HTTP protocols.

In yet another embodiment, the healthcare device 10 is an instrument for analyzing fecal blood for the detection of colon cancer. The web server 14 enables universal access to the obtained measurements using HTML and HTTP protocols.

The following is an example HTML file generated by the web server 14 in response to an HTTP GET command in an embodiment wherein the healthcare device 10 is a blood analyzer.

<TITLE>Blood Analyzer Web Page</TITLE>
<H1>Web page for healthcare device 10</H1>
<HR>
<table border>
<caption>Glucose Measurments </caption>
<TR>
<TD>Patient I.D.</TD>123456</TD>
</TR>
<TR>
<TD>Glucose</T1><TD>12</TD>
</TR>
<TR>
<TD>Time-Stamp</TD><TD>Dec. 1, 1996 12:37</TD>
</TR>
</TABLE>
<HR>

Figure 2:
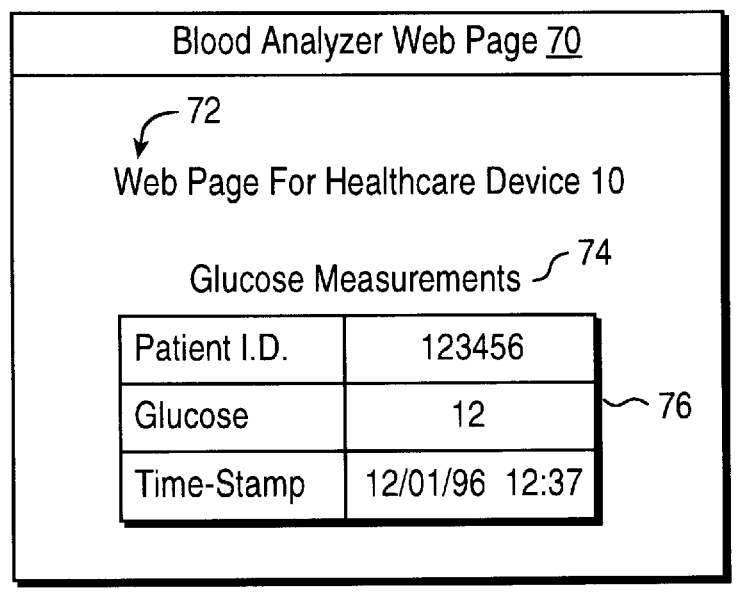
FIG. 2 illustrates a web page rendered by a web browser for an example HTML file that transports medical information from a healthcare device.

FIG. 2 illustrates a web page rendered by the web browser 40 for the example HTML file shown above. The web page for the example blood analyzer device 10 includes a page title 70, a header section 72, a table section 76 containing the medical information obtained from the blood analyzer device 10, and a table header 74.

The medical information shown including Patient I.D. of 123456, Glucose of 12, and Time-Stamp of Dec. 10, 1996 12:37 was generated in the blood analyzer device 10 and packaged into the HTML file shown above by the web server 14. The decoding and rendering of the web page shown is a function of the web browser 40 according to standard formatting protocols for HTML files.

The web server 14 may also implement any one of a variety of methods for providing secure access to the medical measurements and related information stored in the healthcare device 10. Such mechanisms include public or private key encryption of the medical data and related information transported in the HTML file generated by the web server 14.

In addition, access to the healthcare device 10 may be password protected and may require that a smartcard be used at the web browser 40 to enable access. For example, the HTTP command used to request the medical information may be required to include a predetermined password. The web server 14 examines the password and either ignores the HTTP command or transfers a reject message to the requesting web client if the password is missing or invalid.

Figure 3:
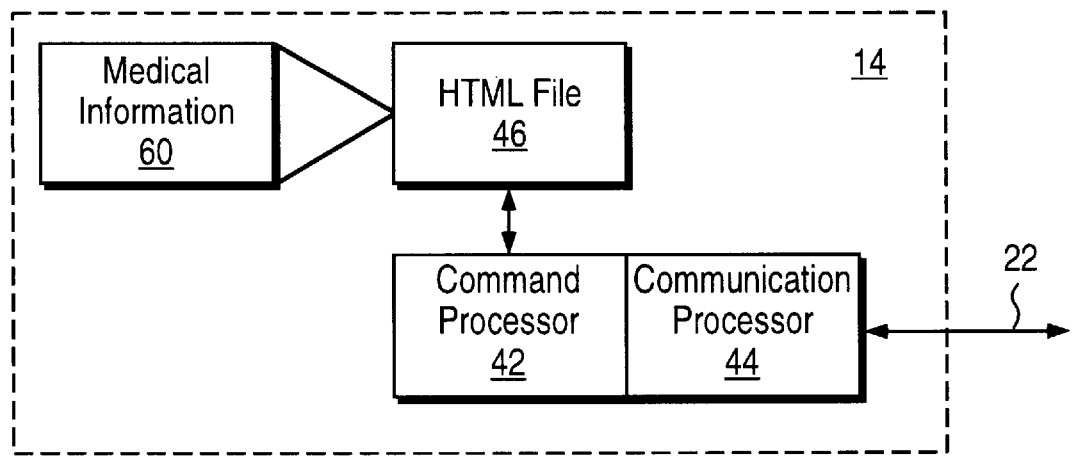
FIG. 3 illustrates a web server in a healthcare device which includes a command processor and a communication processor.

FIG. 3 illustrates the web server 14 which includes a command processor 42 and a communication processor 44. The communication processor 44 is a combination of hardware and software for transferring messages via the communication path 22 using the HTTP protocol. The communication processor 44 relays received HTTP commands from requesting web clients onto the command processor 42.

The command processor 42 is a combination of hardware and software that generates an HTML file 46 and writes a set of medical information 60 obtained in the healthcare device 10 into the HTML file 46. The medical information 60 is generated by the healthcare device 10 according to its predetermined device-specific function for the particular embodiment. The communication processor 44 transfers the HTML file 46 with the medical information 60 to the requesting web client using the HTTP protocol.

In one embodiment, the command processor 42 generates the HTML file 46 on the fly in response to an HTTP command from a requesting web client. This embodiment offers the advantage of not requiring that memory space be allocated in the medical device 10 for storing the HTML file 46.

In another embodiment, the command processor 42 obtains the medical information 60 and then generates the HTML file 46 prior to receipt of an HTTP command from a requesting web client.

Figure 4:
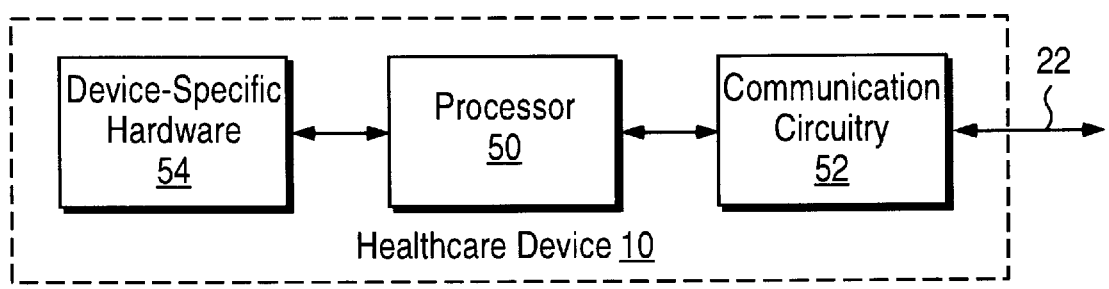
FIG. 4 illustrates one hardware embodiment of the healthcare device which includes a processor, a set of communication circuitry, and a set of device-specific hardware.

FIG. 4 illustrates one hardware embodiment of the healthcare device 10 which includes a processor 50, a set of communication circuitry 52, and a set of device-specific hardware 54. The processor 50 includes memory for storing data and software code. Alternatively, a separate memory may be provided to store data and software code.

The device-specific hardware 54 represents the mechanisms necessary to perform the device-specific medical function of the healthcare device 10. Such mechanisms may include chemical, mechanical, electrical, or electronic mechanisms or any combination thereof. The device-specific hardware 54 may also include the electronic circuitry for digitizing and storing obtained measurements and for displaying the obtained measurements with a display mechanism in the healthcare device 10. Alternatively, the functions of digitizing and storing measurement data may be implemented with the processor 50.

In one embodiment, the processor 50 performs device-specific functions for the healthcare device 10 in combination with the device-specific hardware 54. For example, the processor 50 may execute code for determining blood glucose levels using chemical sensing mechanisms provided by the device-specific hardware 54. The processor 50, the same processor used for device-specific functions, also executes code for performing functions associated with the web server 14 such as obtaining the medical information 60 from the device-specific hardware 54 and generating the HTML file 46 and performing HTTP communication via the communication path 22 including TCP/IP layers.

In other embodiments, the processor 50 may be added to the healthcare device 10 to perform the command processor 42 and communication processor 44 functions of the web server 14 while a separate processor in the device-specific hardware 54 performs the device-specific medical functions.

The communication circuitry 52 enables communication via the communication path 22 using the HTTP open standard protocol. The communication circuitry 52 may be circuitry for communicating over local area networks, or telephone lines including cellular telephone links, or serial communication links, or parallel communication links, or power line communication links, or radio, cellular radio, paging or infrared communication links as is appropriate to a particular embodiment. The communication circuitry 52 in one embodiment includes a processor and code for communicating using the HTTP protocol and underlying TCP/IP communication protocols. In other embodiments, such protocol handling may be provided by the processor 50 with associated executable code.

The foregoing detailed description of the present invention is provided for the purposes of illustration and is not intended to be exhaustive or to limit the invention to the precise embodiment disclosed. Accordingly, the scope of the present invention is defined by the appended claims.

What is claimed is:

1. A method for accessing medical information in a healthcare device, comprising the steps of:

receiving an HTTP command from a web client wherein the command includes a URL that corresponds to the healthcare device;

generating an HTML file that contains the medical information and transferring the HTML file to the web client in response to the HTTP command such that the HTML file is generated on the fly thereby not using memory space in the healthcare device.

2. The method of claim 1, further comprising the step of encrypting the medical information contained in the HTML file.

3. The method of claim 1, wherein the step of transferring the medical information is performed only if the HTTP command includes a predetermined password.

4. A portable healthcare device, comprising:

a communication path;

an existing processor and an existing memory;

a set of device-specific hardware for generating a set of medical information; and a server which is implemented using the existing processor and the existing memory such that the server encrypts and transfers the medical information via the communication path in response to a command received via the communication path using an open standard network protocol on the communication path wherein the medical information is carried in a file having a format that conforms to the open standard network protocol and wherein the server generates the file on the fly such that the file does not use space in the existing memory.

5. The portable healthcare device of claim 4, wherein the command is an HTTP command and the file is an HTML file containing the medical information.

6. The portable healthcare device of claim 4, wherein the server transfers the file containing the medical information only if the command includes a predetermined password.

7. The portable healthcare device of claim 4, wherein the existing processor and the existing memory are also used to implement the open standard network protocol on the communication path.

8. A healthcare device, comprising:

a set of device-specific hardware for generating a set of medical information;

a communication path; and a server coupled to the communication path that obtains the medical information from the device-specific hardware and transfers the medical information via the communication path using an open standard network protocol on the communication path wherein the medical information is carried in a file having a format that conforms to the open standard network protocol and wherein the server generates the file on the fly in response to a command received via the communication path such that the file does not use memory space in the healthcare device.

9. The healthcare device of claim 8, wherein the file is an HTML file such that the server obtains the medical information from the device-specific hardware and generates an HTML file that contains the medical information and transfers the HTML file over the communication path in response to the HTTP command received over the communication path that specifies a URL for the medical device.

10. The healthcare device of claim 9, wherein the server includes means for encrypting the medical information contained in the HTML file.

11. The healthcare device of claim 9, wherein the server transfers the HTML file containing the medical information only if the HTTP command includes a predetermined password.

12. The healthcare device of claim 8, wherein the medical information comprises a set of measurement data generated by the device-specific hardware of the healthcare device.

13. The healthcare device of claim 12, wherein the medical information further comprises a patient identifier corresponding to the measurement data.

14. The healthcare device of claim 12, wherein the medical information further comprises a time-stamp corresponding to the measurement data.

15. The healthcare device of claim 12, wherein the measurement data comprises a set of blood analysis data.

16. The healthcare device of claim 12, wherein the measurement data comprises a set of electrocardiogram recorder data.

17. The healthcare device of claim 12, wherein the measurement data comprises a set of lung efficiency data.

18. The healthcare device of claim 12, wherein the measurement data comprises a set of blood pressure data.

19. The healthcare device of claim 12, wherein the measurement data comprises a set of blood glucose data.

20. The healthcare device of claim 12, wherein the measurement data comprises a set of blood alcohol data.

21. The healthcare device of claim 12, wherein the measurement data comprises a set of fecal blood data.

22. The healthcare device of claim 12, wherein the measurement data comprises a set of body weight data.

* * * * *